(12) United States Patent
Arcilla et al.

(10) Patent No.: US 9,375,548 B2
(45) Date of Patent: Jun. 28, 2016

(54) HUMIDIFIER SYSTEM FOR HUMIDIFYING GAS DELIVERED TO A PATIENT

(75) Inventors: Mabini Arcilla, San Diego, CA (US); Smita Garde, Irvine, CA (US); Samir Ahmad, San Diego, CA (US); Michael Anthony Pietrenka, Escondido, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 203 days.

(21) Appl. No.: 13/993,133

(22) PCT Filed: Dec. 9, 2011

(86) PCT No.: PCT/IB2011/055586
§ 371 (c)(1),
(2), (4) Date: Jun. 11, 2013

(87) PCT Pub. No.: WO2012/080923
PCT Pub. Date: Jun. 21, 2012

(65) Prior Publication Data
US 2013/0263845 A1    Oct. 10, 2013

Related U.S. Application Data

(60) Provisional application No. 61/424,347, filed on Dec. 17, 2010.

(51) Int. Cl.
*A61M 11/00* (2006.01)
*A61M 16/16* (2006.01)
(Continued)

(52) U.S. Cl.
CPC .............. *A61M 16/16* (2013.01); *A61M 11/005* (2013.01); *A61M 11/006* (2014.02); *A61M 11/042* (2014.02); *A61M 16/109* (2014.02); *A61M 16/1075* (2013.01); *A61M 16/1085* (2014.02); *A61M 16/1095* (2014.02); *A61M 16/142* (2014.02); *A61M 15/0085* (2013.01);
(Continued)

(58) Field of Classification Search
CPC ............ A61M 16/109; A61M 16/142; A61M 16/1095; A61M 16/1085; A61M 16/162; A61M 15/10085; A61M 11/006; A61M 11/142; A61M 2205/3653; A61M 2205/3368; A61M 2205/7536
USPC ..................................................... 128/204.17
See application file for complete search history.

(56) References Cited

U.S. PATENT DOCUMENTS 3,949,743 A    4/1976    Shanbrom
4,038,980 A    8/1977    Fodor
(Continued)

FOREIGN PATENT DOCUMENTS

DE    4312793 A1    10/1994
DE    19621541 C1    4/1997
(Continued)

*Primary Examiner* — Justine Yu
*Assistant Examiner* — Douglas Sul

(57) ABSTRACT

Provided are systems and methods for humidifying gas to be provided to a patient utilizing heating of an aerosolized mist. A humidification unit (201a) is provided a patient circuit (209) that provides gas to a patient. The humidification unit includes a liquid chamber (303) that receives liquid from a liquid source (203), a nebulizer (305) that nebulizes liquid from the liquid chamber, an aerosol chamber (307) that receives aerosolized liquid from the nebulizer, and a heat source (309a) that converts the aerosolized liquid into a vapor that humidifies gas in the patient circuit.

12 Claims, 4 Drawing Sheets

(51) Int. Cl.
  *A61M 16/10* (2006.01)
  *A61M 11/04* (2006.01)
  *A61M 16/14* (2006.01)
  *A61M 15/00* (2006.01)

(52) U.S. Cl.
  CPC ...... *A61M16/162* (2013.01); *A61M 2205/3368* (2013.01); *A61M 2205/3653* (2013.01); *A61M 2205/7536* (2013.01)

(56) References Cited

U.S. PATENT DOCUMENTS

| | | | |
|---|---|---|---|
| 4,201,204 A | | 5/1980 | Rinne |
| 5,970,210 A | * | 10/1999 | Anthony ..................... 392/386 |
| 6,367,472 B1 | | 4/2002 | Koch |
| 2002/0170559 A1 | | 11/2002 | Nitta |
| 2003/0196660 A1 | * | 10/2003 | Haveri ..................... 128/203.12 |
| 2004/0231668 A1 | | 11/2004 | Kates |
| 2009/0241948 A1 | * | 10/2009 | Clancy et al. ............ 128/203.14 |
| 2010/0083965 A1 | * | 4/2010 | Virr et al. ................. 128/203.26 |

FOREIGN PATENT DOCUMENTS

| | | |
|---|---|---|
| EP | 0376584 A2 | 7/1997 |
| EP | 1066850 A1 | 1/2001 |
| JP | 2000500988 A | 2/2000 |
| WO | 9707845 A1 | 3/1997 |
| WO | 2009037863 A1 | 3/2009 |
| WO | 2009118718 A1 | 10/2009 |
| WO | 2010035251 A2 | 4/2010 |

* cited by examiner

HUMIDIFIER SYSTEM FOR HUMIDIFYING GAS DELIVERED TO A PATIENT

BACKGROUND

1. Field of the Disclosure

The invention relates to systems and methods for providing humidification of gas utilizing heating of an aerosolized mist.

2. Description of the Related Art

Some conventional methods for humidifying gas for delivery to a patient utilize a chamber. The water chamber holds a quantity of water that is heated using a heating element. Dry gas is fed into the chamber, where it is humidified. The humidified gas then exits the chamber and is delivered to a patient circuit, which ultimately delivers the humidified gas to a patient. FIG. 1A illustrates an example of a water chamber humidifier 100, including a water chamber 101, a heating element 103, a gas inlet 105, and a gas outlet 107.

Use of a water chamber for humidification poses several drawbacks. For example, the water chamber itself can be unwieldy and therefore is typically located away from a patient (e.g., on a ventilator stand). As such, a conduit must be used to deliver humidified gas from the water chamber to a patient circuit. This arrangement leads to condensation in the humidifier conduits, adds significant resistance and compliance in a patient circuit with a humidifier, utilizes a significant amount of power (which typically requires an independent power supply), and poses other difficulties. Furthermore, this arrangement can be cumbersome for use during patient transport, during home use, and in other situations, due to the unwieldy water chamber and large power demands.

Other conventional methods for humidifying gas include the use of a passive heat and moisture exchanger (HME). FIG. 1B illustrates an HME 150 that includes a conduit 151 and a hydrophilic foam filter 153. Dry gas may be provided to the foam filter 153, which contains water therein, therefore humidifying the gas, which is provided to a patient. While an HME can be placed in a patient circuit, it does not reliably provide adequate humidification.

These and other problems exist.

SUMMARY

In some embodiments a humidifier system is provided for humidifying gas that is delivered to a patient. The humidifier system may comprise a liquid source and a humidification unit. The humidification unit may be disposed on a patient circuit that provides gas to a patient. The humidification unit may comprise a liquid chamber that receives liquid from the liquid source, a nebulizer that nebulizes liquid from the liquid chamber, an aerosol chamber that receives aerosolized liquid from the nebulizer, and a heat source that converts the aerosolized liquid into a vapor that humidifies gas in the patient circuit.

In some embodiments, the humidification unit further includes a hydrophobic membrane that separates the aerosol chamber from the patient circuit, such that the hydrophobic membrane prevents liquid from entering the patient circuit from the aerosol chamber but permits vapor to enter the patient circuit from the aerosol chamber.

In some embodiments, the heat source of the humidification unit is located on a wall of the aerosol chamber. In some embodiments, the heat source of the humidification unit is located at a location along a path from the aerosol chamber to the patient circuit. In some embodiments, the heat source of the humidification unit is located within the patient circuit.

In some embodiments, a method is provided for humidifying gas delivered to a patient. The method may include receiving, at a liquid chamber, water from a liquid source, aerosolizing liquid from the liquid chamber, providing the aerosolized liquid to an aerosol chamber, heating the aerosolized liquid into a vapor; and providing the vapor to a patient circuit to humidify a gas therein. In some embodiments, a hydrophobic membrane separates the aerosol chamber from the patient circuit such that liquid is prevented from entering the patient circuit from the aerosol chamber and the vapor is permitted to enter the patient circuit from the aerosol chamber.

In some embodiments, the aerosolized liquid is heated into the vapor from a heat source that is located on a wall of the aerosol chamber. In some embodiments, the aerosolized liquid is heated into the vapor from a heat source that is located at a location along a path from the aerosol chamber to the patient circuit. In some embodiments, the aerosolized liquid is heated into the vapor from a heat source that is located within the patient circuit.

In some embodiments, a humidifier system may be provided for humidifying gas delivered to a patient. The humidification system may comprise liquid source means for storing a liquid and humidification means disposed on a patient circuit that provides gas to a patient. The humidification means comprises liquid chamber means for receiving liquid from the liquid source means, nebulizing means for nebulizing liquid from the liquid chamber means, aerosol chamber means for receiving aerosolized liquid from the nebulizing means, and heat source means for converting the aerosolized liquid into a vapor that humidifies gas in the patient circuit.

In some embodiments, the humidification means further includes a membrane means for separating the aerosol chamber means from the patient circuit, such that liquid is prevented from entering the patient circuit from the aerosol chamber means, but the vapor is permitted to enter the patient circuit from the aerosol chamber means.

In some embodiments, the heat source means of the humidification means is located on a wall of the aerosol chamber means. In some embodiments, the heat source means of the humidification means is located at a location along a path from the aerosol chamber means to the patient circuit. In some embodiments, the heat source means of the humidification means is located within the patient circuit.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not a limitation. In addition, it should be appreciated that structural features shown or described in any one embodiment herein can be used in other embodiments as well. It is to be expressly understood, however, that the drawings are for the purpose of illustration and description only and are not intended as a definition of limits. As used in the specification and in the claims, the singular form of "a", "an", and "the" include plural referents unless the context clearly dictates otherwise.

BRIEF DESCRIPTION OF THE DRAWINGS

FIG. 1A illustrates an example of a conventional chamber humidifier.

FIG. 1B illustrates an example of a conventional passive heat and moisture exchanger.

DETAILED DESCRIPTION OF THE EXEMPLARY EMBODIMENTS

Embodiments described herein may enable humidification of gas for patients with reduced power consumption as compared to some conventional humidifiers, Furthermore the embodiments described herein may eliminate condensation or water in humidifier conduits or patient circuits. The embodiments described herein may further provide for humidifiers having a small, compact and lightweight design, which along with reduced power consumption enables use during patient transport, integration with ventilator systems, use in NICU (neonatal intensive care unit) and home applications, and/or provide other advantages.

Figure 1A:
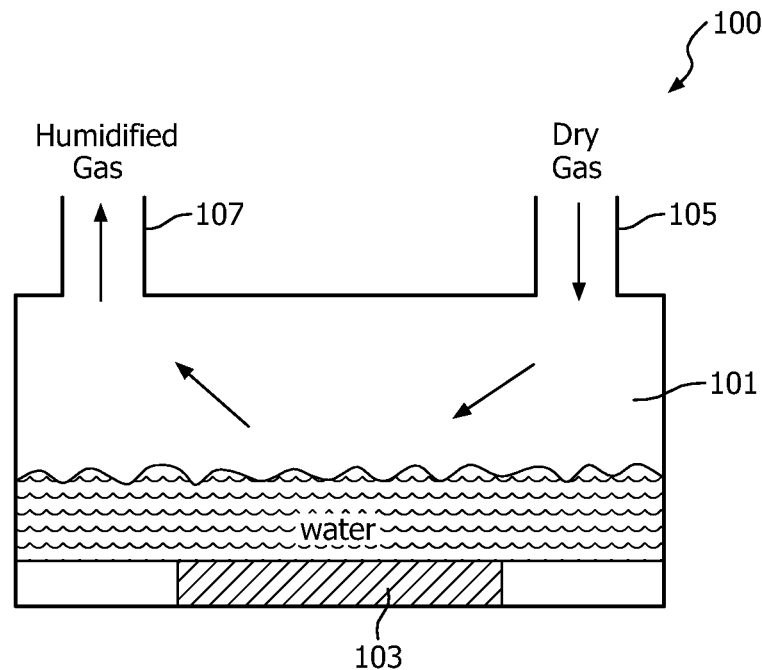
Figure 1B:
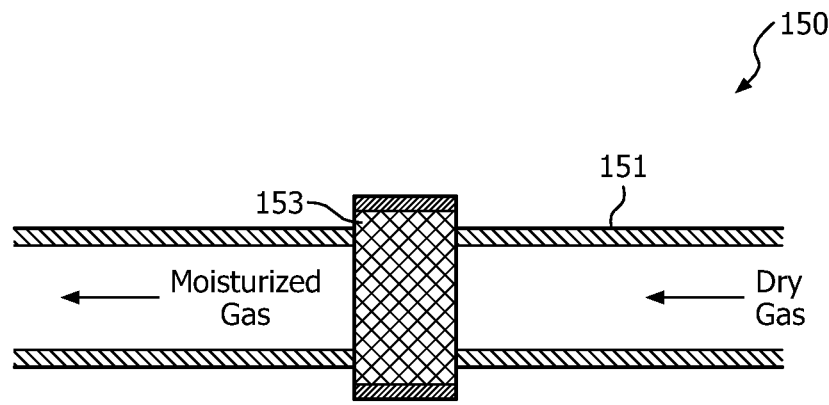
Figure 2:
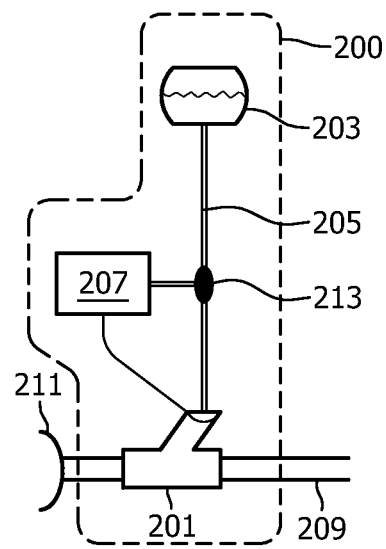
FIG. 2 illustrates an example of a humidifier system according to various embodiments of the invention.

FIG. 2 illustrates a humidifier system 200, which is an example of a humidifier system for providing humidified gas to a patient. In some embodiments, humidifier system 200 includes a humidification unit 201, a liquid source 203, a supply portion 205, a controller 207, and or other elements.

Humidification unit 201 may be positioned along a patient circuit 209 that delivers humidified gas to a patient via a patient interface 211. In some implementations, in some embodiments, humidification unit 201 may be positioned along patient circuit 209 proximal to patent patient interface 211. For example, in some implementations humidification unit 201 may be placed on patient circuit 209 between 6 to 8 inches from patient interface 211. In some embodiments, humidification unit 201 may be placed on an elbow of a mask or other patient interface 211 that is used in noninvasive ventilation. Other distances and/or placements may be used. Conventional humidifiers mounted on ventilator carts are typically placed 4 to 6 feet away from the patient. This distance can lead to condensation in the conduits connecting the ventilator to a patient circuit, which can lead to inadequately humidified gas. Solutions to this problem such as, for example, wire-heated conduits, introduce additional complexity and power needs to the system and may also adversely affect the humidity and temperature of gas delivered to a patient.

Patient circuit 209 may include or be a part of a system that creates a flow of gas toward the patient for introduction into the patient's respiratory system. For example, in some implementations, patient circuit 209 may be part of a ventilator system (not illustrated). Patient interface 211 of patient circuit 209 may include a nasal and/or oral mask, a nasal cannula, an invasive tube, and/or other interface with a patient's respiratory system.

Liquid source 203 may include a container (e.g., bag, canister, etc) of fluid that can be aerosolized and is suitable for humidifying gas to be provided to the respiratory system of a patient. In some embodiments, the liquid may be water. In some embodiments, the liquid may be water containing one or more additives or may be any fluid that can be aerosolized and that is suitable for humidifying gas to be delivered to a patient. In some implementations, liquid source 203 is connected to humidification unit 201 via a supply portion 205, which may be or include flexible tubing or other conduit capable of transporting fluid from liquid source 203 to humidification unit 201. Water may be supplied to humidification unit 201 by a gravity feed, a pump (not illustrated) or other method that maintains a pressure above airway pressure.

Humidifier system 200 may also include a valve 213 (e.g., a pinch valve) disposed along supply tube or elsewhere in system 200 for controlling the flow of liquid from liquid source 203 to humidification unit 201. Additionally, one or more sensors (e.g., temperature sensors, humidity sensors, flow sensors, and/or other sensors) may be part of or used with system 200.

Controller 207 may include an electronic and/or computer-implemented device that controls one or more aspects of humidifier system 200. In some embodiments, controller 107 may include one or more micro-processors, associated memory, and/or other computer components for performing various computing tasks, including control of heat sources, control of nebulizers, control of valves, receipt of data from sensors, receipt of instructions/data from users, performance of calculations/determinations, and/or other tasks. The one or more processors of controller may be programmed using one or more modules that comprise processor-executable instructions for humidifying gas as described herein. In some embodiments, controller 207 may be part of or otherwise associated with a controller of a device that provides other features (e.g., a ventilator).

It will be understood to those having skill in the art that humidifier system 200 may include or be connectable to any power supply (e.g., batteries, AC connection) necessary for the operation of controllers, nebulizers, heat sources, valves, sensors, pumps, or other components of humidifier system 200.

Figure 3A:
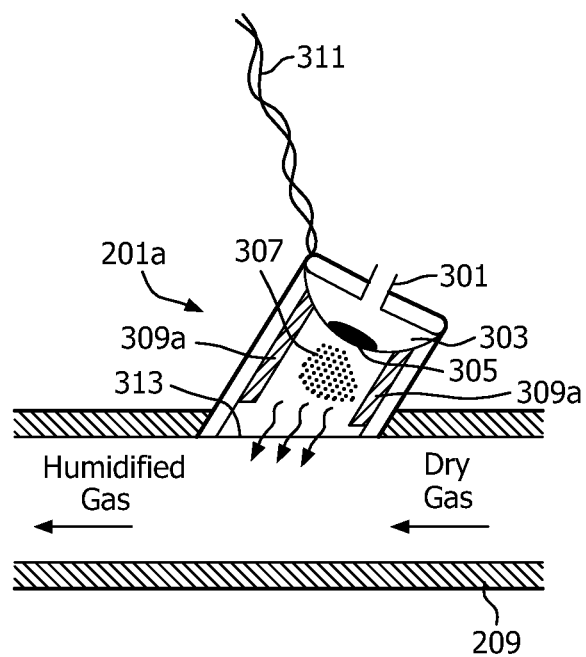
FIG. 3A illustrates an example of a humidification unit according to various embodiments of the invention.
Figure 3B:
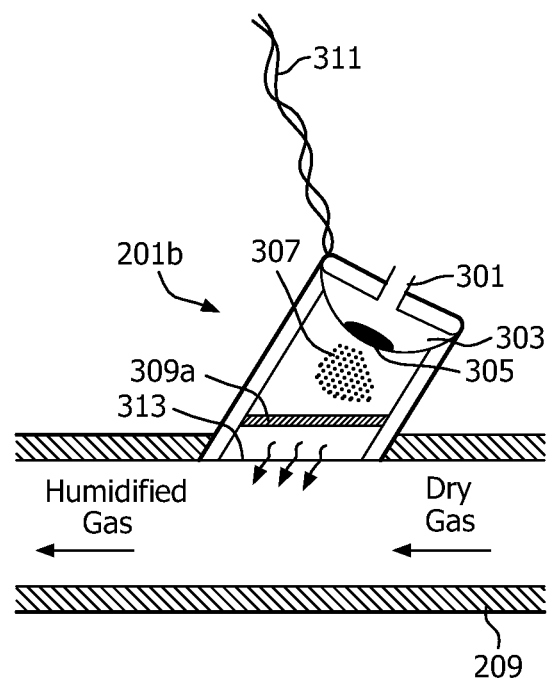
FIG. 3B illustrates an example of a humidification unit according to various embodiments of the invention.
Figure 3C:
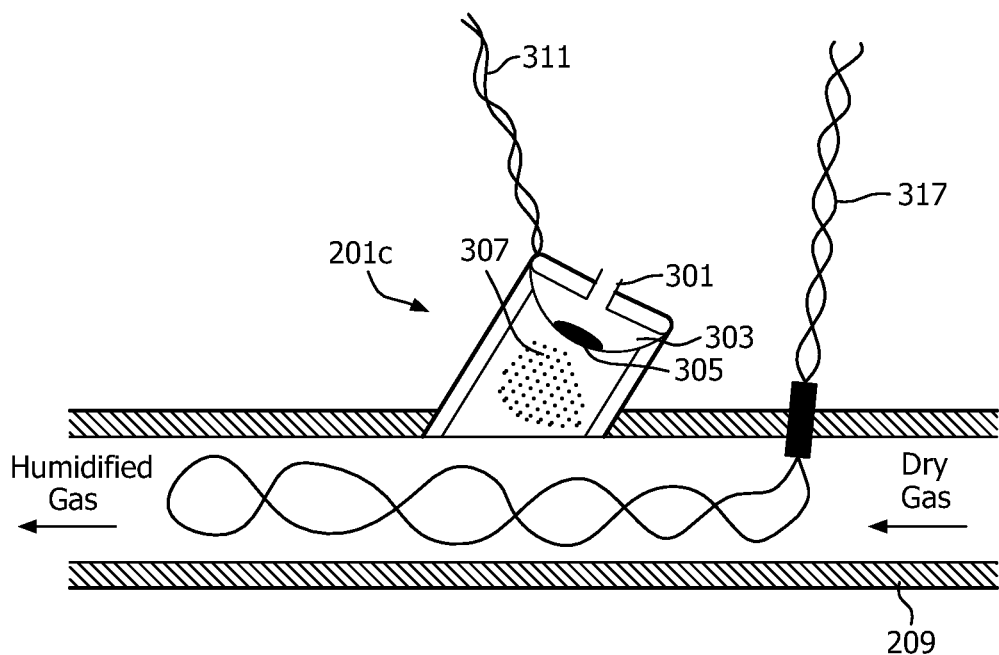
FIG. 3C illustrates an example of a humidification unit according to various embodiments of the invention.
Figure 4:
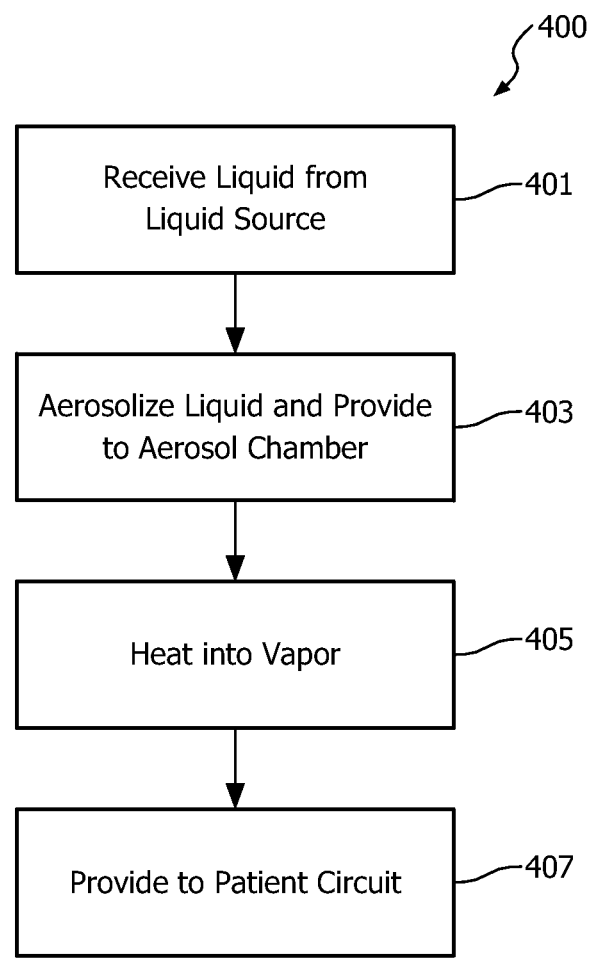
FIG. 4 illustrates an example of a process for humidifying gas according to various embodiments of the invention.

FIG. 3A illustrates a cross-section of humidification unit 201a, which is an example of a humidification unit that may be used in humidification system 200. In some embodiments, humidification unit 201a may include a liquid inlet 301 which may be part of or may connect to supply tube 205 or otherwise connect to liquid source 203. Humidification unit 201a may also include a liquid chamber 303, which receives liquid from liquid inlet 301. In some embodiments, liquid may enter liquid chamber in drops via a drip-wise connection. Other connections and flow types may also be used. Humidification unit 201a may also include a nebulizer 305 that nebulizes liquid from liquid chamber 303 into an aerosol chamber 307. In some embodiments, nebulizer 305 may include an aperture plate or mesh with one or more small holes (e.g., average of~2 μm) that is connected to a vibrational element (e.g., a piezoelectric element or an ultrasonic horn driven by a piezoelectric element). Vibration of the vibrational element causes the mesh or aperture plate to vibrate, which causes liquid to move through the holes and into aerosol chamber 307, converting the liquid to aerosolized particles (i.e., nebulizing the liquid). In some implementations, the vibrational element may include piezoelectric element. In some implementations, the piezoelectric element may comprise the aperature plate having the holes and one or more holes. In some embodiments, nebulizer 305 may include a pressure-based nebulizer that forces otherwise through an orifice so as to nebulizer liquid in liquid chamber and propel it into aerosol chamber 307.

In some embodiments, liquid chamber 303 may include a concave or bowl shaped bottom portion or floor. Nebulizer 305 may be located at the bottom of this floor so that liquid introduced into liquid chamber 303 is funneled towards nebulizer. liquid chamber may also include a top cover that include liquid inlet 301 but otherwise seals liquid chamber 303 from the ambient environment. In some embodiments, other configurations may be used.

Humidification unit 201a may also include a heater 309a, located in aerosol chamber 307, which may convert aerosolized liquid in aerosol chamber 307 into a gas/vapor (e.g., water vapor). Less power consumption may be needed to convert aerosolized liquid into a vapor than is necessary to convert non-aerosolized liquid into a vapor. The mass median aerodynamic diameter (MMAD) of aerosolized particles typically ranges between 1 μm to 5 μm. Heater 309*a* may be for example, a PTC (positive temperature coefficient) ceramic heater element, insulated etched foil heater, insulated wound wire heater, carbon fiber heater, or other heating element suitable for use in medical applications. Heater 309*a* and/or nebulization portion 305 may include connectors 311 which may be wires or other connectors to provide power and/or an operative connection to controller 207. In some embodiments, aerosol chamber 307 may be a cylindrical chamber (FIGS. 3A-C illustrating a cross section lengthwise through the cylinder). However, other configurations may be used. As illustrated in FIG. 3A, heater 309*a* may line the walls of aerosol chamber 307 and therefore encircle the aerosolized liquid. In some embodiments, heater 309*a* may include one or more discontinuous panels or elements which may provide sufficient heat to convert aerosolized liquid into a vapor.

Humidification unit 201*a* may include a membrane 313 which may separate aerosol chamber 307 from patient circuit 209. In some embodiments, membrane 313 may comprise a hydrophobic membrane that is impermeable to liquid but permeable to the vapor (e.g., a membrane made using a polyterafluoroethylene [PTFE] base material). As such, liquid (including aerosolized water) cannot enter patient circuit 209 from aerosol chamber 307, but vaporized liquid can enter, thereby humidifying the gas in patient circuit 209.

FIG. 3B illustrates a cross section of humidification unit 201*b*, which is an example of a humidification unit that may be used with humidification system 200. Humidification unit 201*b* includes a liquid inlet 301, a liquid chamber 303, a nebulization portion 305, an aerosol chamber 307, connectors 311, and membrane 313. Humidification unit 201*b* may also include a heater 309*b*, which may be located in aerosol chamber 307 between nebulizer 305 and membrane 313. Heater 309*b* may be located at a location along a path within aerosol chamber 307 between liquid chamber 303 and patient circuit 209. As such, heater 309*b* may generally obstruct flow along this path. However, heater 309*b* may be or include a porous element (e.g., a ceramic or carbon fiber heating element) that may enable aerosolized liquid to pass therethrough. As such, heater 309*b* heats and thus converts aerosolized liquid to a vapor as (or immediately before) the aerosolized liquid passes through the pores of heater 309*b*.

FIG. 3C illustrates a cross-section of humidification unit 201*c*, which is an example of a humidification unit that may be used with humidification system 200. Humidification unit 201*c* includes a liquid inlet 301, a liquid chamber 303, a nebulization portion 305, an aerosol chamber 307, and connectors 311. Humidification unit 201*c* may also include a heating element 315 disposed in patient circuit 209. Heating element 315 may be a wire or other heat-generating element that is placed inside of patient circuit 209. In some implementations, humidification unit 201*c* may be located farther away from patient interface 211 and closer to an associated ventilator unit (i.e., it may not be proximally located to the patient interface). Furthermore, in some embodiments, humidification unit 201*c* may include no membrane. Therefore, aerosolized liquid may freely enter patient circuit 209 at a location away from the patient and closer to a ventilator, where it is converted to vapor by heat from heating element 315. Heating element may be connected to controller 207 and/or a power source by connectors 317. Humidification unit 201*c* may be located farther away from the patent interface so that the heat from heating element 315 provides adequately heated and humidified gas to the patient.

FIG. 4 illustrates a process 400, which is an example of a process for humidifying gas for delivery to a patient. Process includes an operation 401, wherein liquid is received, from a liquid source (e.g., liquid source 203), into a liquid chamber (e.g., liquid chamber 303). In an operation 403, the liquid in the liquid chamber is aerosolized (e.g., using nebulizer 305) and provided to an aerosol chamber (e.g., aerosol chamber 307). In an operation 405, the aerosolized liquid may then be heated into a vapor (e.g., using heat source 309*a*, 309*b*, heating element 315, heated gas). In an operation 407, the vapor may be provided to a patient circuit (e.g., patient circuit 209) so as to humidify gas in the patient circuit. As described herein, in some instances, the aerosolized liquid may be heated and converted to vapor in the patient circuit.

As discussed herein, the use of aerosolized liquid for humidification with a proximally located humidifier provides several benefits, including: less power use for vaporizing liquid, compact and efficient design, faster response rate (as smaller volume of liquid is needed) and/or other benefits. Furthermore, the embodiments described herein add minimal compliance, resistance, and dead-space in patient circuit. Table 1 illustrates comparative resistance or pressure drop and compliance or volume of a representative passive heat and moisture exchanger (HME)and a representative conventional water chamber humidifier as compared to an aerosolized proximal humidifier as described herein.

TABLE 1

| Flow (slpm) | HME Device (cmH2O) | Water Chamber Device (cmH2O) | Aerosolized Humidifier (cmH2O) |
|---|---|---|---|
| | Pressure Drop Across Humidifier | | |
| 10 | 0.15 | 0.3 | 0.0 |
| 30 | 0.56 | 0.13 | 0.0 |
| 60 | 1.25 | 0.48 | 0.15 |
| 120 | 3.19 | 1.85 | 0.6 |
| | Humidifier Compliance | | |
| Volume | 90 ml | 350 ml | 19 ml |

The embodiments described herein can be used for various therapies that require the humidification and heating of gasses for home or hospital use, including: invasive ventilation, non-invasive ventilation, high flow oxygen therapy, neonatal CPAP (continuous positive airway pressure), home CPAP (e.g., for adult apnea), high frequency ventilation and/or other therapies/uses. In some implementations, a humidifier system 100 may be used with patient circuits having various tubing sizes (e.g., 22 mm, 15 mm, 10 mm, or other size) to support adult, pediatric, or neonatal humidification. In some embodiments, humidifier system 100 (or the various humidification units described herein) may be used as a stand-alone humidifier with an independent heating and humidification control unit. In some embodiments, humidifier system 100 (or the various humidification units described herein) may be integrated with another system (e.g., ventilator) enabling integrated power, control, alarms, and/or other features.

The system and methods described herein are provided as examples only. Those having skill in the art will appreciate that the systems described herein may work with various system configurations. Accordingly, more or less of the aforementioned system components may be used and/or combined in various implementations. It should also be understood any software modules that are utilized to accomplish the functionalities described herein may be maintained on other components than those described herein. In some implementations, as would be appreciated, the functionalities described herein may be implemented in various combinations of hardware and/or firmware, in addition to, or instead of, software. The processes described herein may utilize more or less of the described operations and the order of operations may be altered as would be appreciated.

Embodiments further include non-transitory computer readable media (e.g., discs, memory sticks, hard disks, or other volatile or non-volatile storage media) having computer executable instructions thereon that cause/configure/instruct one or more processors to perform some or all of the features and functions described herein.

Details included herein are for the purpose of illustration based on what is currently considered to be the most practical and preferred embodiments, it is to be understood that such detail is solely for that purpose and that the scope of this specification is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A humidifier system for humidifying gas delivered to a patient, comprising:
    a liquid source; and
    a humidification unit disposed on a patient circuit that provides gas to a patient, wherein the humidification unit comprises:
        a liquid chamber that receives liquid from the liquid source, wherein the liquid chamber includes a concave shaped bottom portion,
        a nebulizer that nebulizes liquid from the liquid chamber, wherein the nebulizer is located at the bottom portion of the liquid chamber so that liquid introduced into the liquid chamber is funneled towards the nebulizer, and wherein the nebulizer comprises an aperture plate with holes, the aperture plate being coupled to a vibrational element, wherein vibration of the vibrational element causes the aperture plate to vibrate, which causes liquid to move through the aperture plate holes for nebulizing the liquid into aerosolized particles,
        an aerosol chamber that receives aerosolized particles from the nebulizer,
        a heat source located within the aerosol chamber that converts the aerosolized particles into a vapor, and
        a hydrophobic membrane that separates the aerosol chamber from the patient circuit, wherein the hydrophobic membrane prevents liquid and aerosolized particles in the aerosol chamber from entering the patient circuit but permits the vapor to enter the patient circuit from the aerosol chamber which humidifies gas in the patient circuit.

2. The system of claim 1, further wherein the heat source includes one or more discontinuous panels or elements located on a wall of the aerosol chamber that provide sufficient heat to convert the aerosolized particles into the vapor.

3. The system of claim 1, further wherein the heat source is located between the nebulizer and the hydrophobic membrane along a path from the aerosol chamber to the patient circuit, wherein the heat source generally obstructs a flow along the path and further comprises a porous element that enables aerosolized particles to pass therethrough, further to heat and convert the aerosolized particles into the vapor.

4. The system of claim 1, further wherein the aerosol chamber comprises walls, and wherein the heat source lines the walls of the aerosol chamber to encircle the aerosolized particles, further to heat and convert the aerosolized particles into the vapor.

5. A method for humidifying gas delivered to a patient, comprising:
    receiving, at a liquid chamber, water from a liquid source, wherein the liquid chamber includes a concave shaped bottom portion;
    aerosolizing liquid from the liquid chamber, wherein aerosolizing liquid comprises providing a nebulizer located at the bottom portion of the liquid chamber so that liquid introduced into the liquid chamber is funneled towards the nebulizer, and wherein providing the nebulizer comprises providing an aperture plate with holes, the aperture plate being coupled to a vibrational element, vibrating the vibrational element to cause the aperture plate to vibrate, which causes liquid to move through the aperture plate holes for nebulizing the liquid into aerosolized particles;
    providing the aerosolized particles to an aerosol chamber;
    heating the aerosolized particles within the aerosol chamber into a vapor;
    separating, via a hydrophobic membrane, the aerosol chamber from a patient circuit, wherein the hydrophobic membrane prevents liquid and aerosolized particles in the aerosol chamber from entering the patient circuit but permits the vapor to enter the patient circuit from the aerosol chamber; and
    providing the vapor to the patient circuit to humidify a gas therein.

6. The method of claim 5, further wherein the aerosolized particles are heated into the vapor from a heat source that includes one or more discontinuous panels or elements located on a wall of the aerosol chamber.

7. The method of claim 5, further wherein the aerosolized particles are heated into the vapor from a heat source that is located between the nebulizer and the hydrophobic membrane along a path from the aerosol chamber to the patient circuit, wherein the heat source generally obstructs a flow along the path and further comprises a porous element that enables aerosolized particles to pass therethrouqh.

8. The method of claim 5, further wherein the aerosol chamber comprises walls, and wherein the aerosolized particles are heated into the vapor from a heat source that lines the walls of the aerosol chamber to encircle the aerosolized particles.

9. A humidifier system for humidifying gas delivered to a patient, comprising:
    liquid source means for storing a liquid; and
    humidification means disposed on a patient circuit that provides gas to a patient, wherein the humidification means comprises:
        liquid chamber means for receiving liquid from the liquid source means, wherein the liquid chamber means includes a concave shaped bottom portion, nebulizing means for nebulizing liquid from the liquid chamber means, wherein the nebulizing means is located at the bottom portion of the liquid chamber means so that liquid introduced into the liquid chamber means is funneled towards the nebulizing means, and wherein the nebulizing means comprises an aperture plate with holes, the aperture plate being coupled to a vibrational element, wherein vibration of the vibrational element causes the aperture plate to vibrate, which causes liquid to move through the aperture plate holes for nebulizing the liquid into aerosolized particles, aerosol chamber means for receiving aerosolized particles from the nebulizing means, heat source means for converting the aerosolized particles into a vapor, wherein the heat source means is located within the aerosol chamber means, and a hydrophobic membrane means for separating the aerosol chamber means from the patient circuit, wherein the hydrophobic membrane means prevents liquid and aerosolized particles in the aerosol chamber means from entering the patient circuit but permits the vapor to enter the patient circuit from the aerosol chamber means which humidifies gas in the patient circuit.

10. The system of claim 9, further wherein the heat source means includes one or more discontinuous panels or elements located on a wall of the aerosol chamber means that provide sufficient heat to convert the aerosolized particles into the vapor.

11. The system of claim 9, further wherein the heat source means is located between the nebulizing means and the hydrophobic membrane means along a path from the aerosol chamber means to the patient circuit, wherein the heat source means generally obstructs a flow along the path and further comprises a porous element that enables aerosolized particles to pass therethrough, further to heat and convert the aerosolized particles into the vapor.

12. The system of claim 9, further wherein the aerosol chamber means comprises walls, and wherein the heat source means lines the walls of the aerosol chamber means to encircle the aerosolized particles, further to heat and convert the aerosolized particles into the vapor.

* * * * *